United States Patent
Ertl

(10) Patent No.: US 8,332,015 B2
(45) Date of Patent: Dec. 11, 2012

(54) METHOD FOR MEASURING A BODY HAVING AT LEAST ONE SEMITRANSPARENT LAYER

(75) Inventor: Thomas Ertl, Dreieich (DE)

(73) Assignee: DeguDent GmbH, Hanau (DE)

( * ) Notice: Subject to any disclaimer, the term of this patent is extended or adjusted under 35 U.S.C. 154(b) by 1109 days.

(21) Appl. No.: 12/238,548

(22) Filed: Sep. 26, 2008

(65) Prior Publication Data

US 2009/0087811 A1 Apr. 2, 2009

(30) Foreign Application Priority Data

Sep. 26, 2007 (DE) .................. 10 2007 046 228

(51) Int. Cl.
*A61B 6/00* (2006.01)

(52) U.S. Cl. ........ 600/476; 600/109; 600/407; 600/477; 600/478

(58) Field of Classification Search .............. 600/109, 600/407, 560, 476, 477, 478
See application file for complete search history.

(56) References Cited

U.S. PATENT DOCUMENTS

| 5,306,144 | A  | * | 4/1994 | Hibst et al. ........... 433/29 |
| 6,201,880 | B1 | * | 3/2001 | Elbaum et al. ........ 382/100 |
| 6,997,883 | B1 | * | 2/2006 | Hahn .................... 600/560 |

FOREIGN PATENT DOCUMENTS

| CH | 658146 | 10/1986 |
| EP | 0962185 | 5/1999 |
| WO | 03094771 | 11/2003 |
| WO | 2007051567 | 5/2007 |

\* cited by examiner

*Primary Examiner* — Brian Casler
*Assistant Examiner* — Joel Lamprecht
(74) *Attorney, Agent, or Firm* — Dennison, Schultz & MacDonald

(57) ABSTRACT

The invention relates to a method for detecting properties or alterations in at least one semitransparent layer of a body of a tooth by applying light escaping from at least one light guide via the front thereof to the body, as well as for recording at least one area of the body by means of a camera and subsequently assessing the image determined by the sensor. In order to be able to detect alterations or properties with high accuracy and a high image quality, it is proposed to place the front of the light guide on the body in order to subject the body to the light of the light guide.

19 Claims, 1 Drawing Sheet

Fig. 1
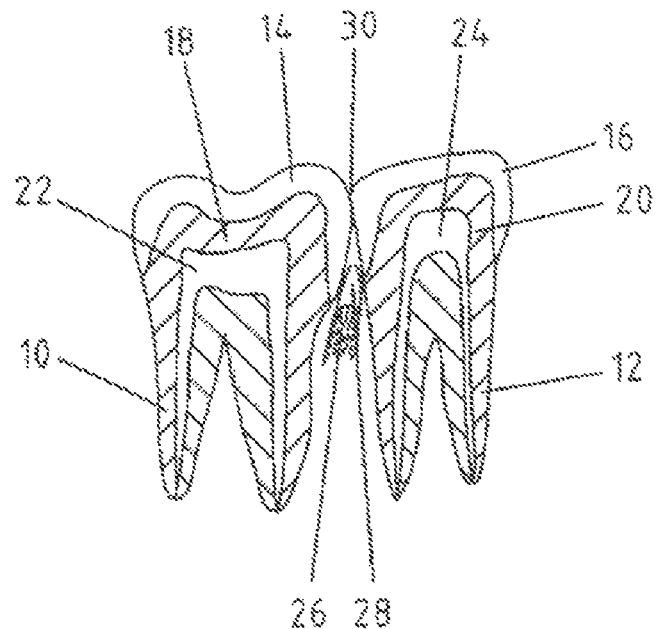
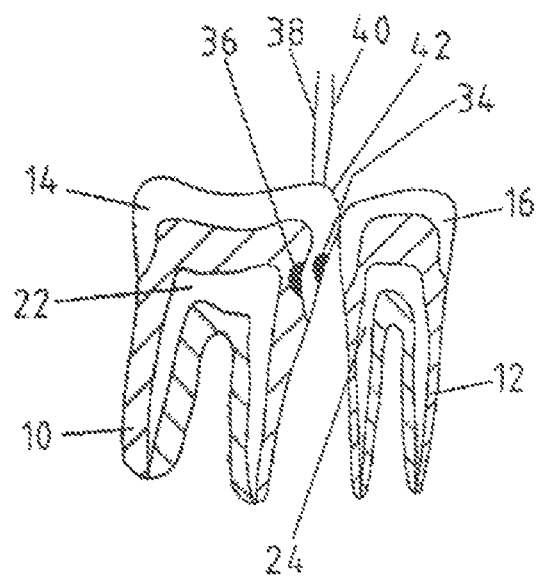
Fig. 2
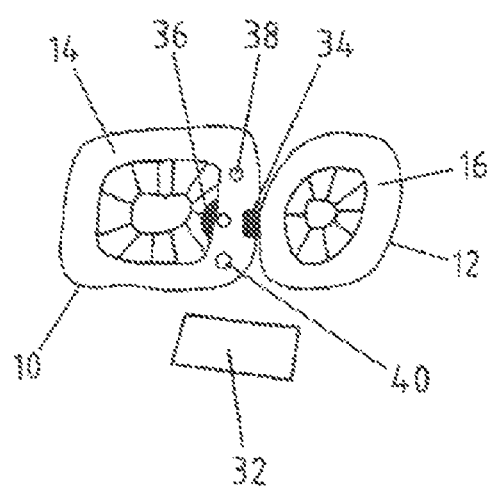
Fig. 3

METHOD FOR MEASURING A BODY HAVING AT LEAST ONE SEMITRANSPARENT LAYER

BACKGROUND OF THE INVENTION

The invention relates to a method for measuring a body having at least one semitransparent layer by applying light escaping from at least one light guide via the front thereof to the body as well as recording at least one area of the body by means of an optical sensor, such as a camera. The invention relates in particular to a method for detecting alterations on at least one tooth in the area of the dentine and/or tooth enamel, in particular in order to detect caries or cracks in the enamel, by applying light escaping from at least one light guide via the front thereof to the tooth as well as recording at least one area of at least one tooth by means of an optical sensor, such as a camera, and subsequently evaluating the image or images determined by the sensor.

SUMMARY OF THE INVENTION

X-ray diagnostics have proven to be useful for the detection of caries. However, since X-ray radiation is increasingly less accepted by patients, there is a need for alternative imaging processes without ionizing radiation, especially for interproximal caries diagnostic, that is, caries in the approximal space. The dentist frequently performs a visual diagnostic. However, this has the disadvantage that with caries that typically occur just underneath of the contact point of two teeth, that is, where teeth adjoin each other, an alteration is only visually detectable much later.

Non-imaging and imaging methods to avoid the mostly subjective visual diagnostic by the dentist are known.

Arrangements for non-imaging caries detection are currently based on fluorescence measurements in a reflection arrangement (EP 0 962 185 B1) or reflection measurements with different light wavelengths without utilizing fluorescence excitation (WO 03/094771). Light is radiated with a light guide (optical fiber or sapphire prism) onto the tooth surface and the reflected light is guided over the same or another light guide into a light receiver. Photodiodes are typically used as light receivers. Transmitting and receiving light guides have a defined relation to each other in a coaxial arrangement. Light of different spectral composition is detected depending on the condition of the tooth (caries/no caries). Conclusions with regard to the presence of caries and—within narrow limits—the size and penetration depth of the caries can be drawn from the percentage of light reflection within different spectral ranges or fluorescence intensity.

A disadvantage of the non-imaging process is the poor interpretability by the dentist due to missing information regarding the spatial distribution. Merely a numerical value (for example, 0=healthy tooth; 100=highly carious tooth) or limited caries degree differentiation by means of different acoustic signals is made available. The correlation with regard to histologic caries extent is however limited.

The imaging methods include transmission measurements without fluorescence excitation (WO 98/29050; United States patent 2006/02230329 A1). Arrangements are used therein, which are comparable in principle to those used in X-ray diagnostics. The transmitted light of a surface illumination of the tooth is detected by a camera on the opposite side of the tooth. Light in the visible range of the spectrum is used according to WO 98/29050. United States patent 2006/0223032 A1, however, envisions the use of light in the near infrared spectrum. This leads to a clearly improved image quality during transillumination of the tooth enamel.

The image quality is not comparable to that of an X-ray image if light in the visible range is used. For this reason, the use of light in the wavelength range between 1300 nm and 1400 nm has proven valuable. It is a disadvantage, however, that a cost-intensive InGaAs array has to be used as the detector. For cost reasons, commercial use of the corresponding arrangements for caries diagnostic therefore has its limits. It is disadvantageous, in addition, that polarizing filters must be used in order to prevent irradiation of the sensor at sites in which no tooth or gum is located in the beam path.

It is also known to conduct fluorescence measurements in reflection arrangements. For this purpose, the fluorescence image of an intraoral camera for caries diagnostic can be used. The autofluorescence of the hard tooth tissue is measured in a reflection arrangement. A healthy hard tooth tissue, in particular the dentine layer, emits light in the green spectral range under UV light. If any carious areas are present, autofluorescence is considerably reduced. Corresponding processes can be used in order to detect fissure caries and smooth surface caries outside the approximal space. A diagnostic cannot be carried out for interproximal caries detection, that is, caries within the approximal space, because of the missing reflection. Independently thereof, the known imaging processes for caries detection have in common that a wide-range illumination source is used, which simultaneously illuminates the entire tooth or at least a large part of the tooth or if required several teeth.

In addition to the optical techniques mentioned above, impedance measurements for caries diagnostic are also used, however they are associated with disadvantages regarding sensitivity due to the degree of moisture of the tooth.

It is an object of the present invention to refine a method of the kind disclosed above in such a way that alterations on/in at least one semitransparent object, in particular a tooth, and in this special case caries, such as fissure caries or smooth surface caries, in particular caries in the approximal space, can be detected with high accuracy, and high image quality can be achieved, making an evaluation possible that corresponds for the most part to that which can be achieved with X-ray radiation, without having to accept the disadvantages of X-ray radiation.

The object of the invention is attained substantially in that, for applying light of the at least one light guide to the body, the front of the light guide is placed on the body, or positioned at a distance a, with a≦2d and d=light guide core diameter, from the surface of the body in such a way that light reflected by the body surface is exclusively, or substantially exclusively, reflected back into the light guide, and that scattered light escaping from the body is measured with the optical sensor. The object is attained in particular in that, for applying the light of the at least one light guide to the at least one tooth, the front of the light guide is placed on the at least one tooth, or positioned at a distance from the surface of the at least one tooth, such that radiation reflected by the tooth surface is exclusively, or substantially exclusively, reflected back into the light guide, wherein when the front of the light guide is positioned at a distance from the tooth, the front is at a distance a≦2d, with d=light guide core diameter, and scattered light escaping from the tooth is measured with the optical sensor.

According to the teaching of the invention, a locally narrowly defined light injection into the at least one body, such as a tooth, is carried out, whereby light distribution that corresponds to the optical properties of the body, such as a tooth, develops in the tooth volume, and can then be observed with the optical sensor in at least one position that is different from the light injection point. The radiation reflected by the body surface, such as the tooth surface, travels back into the light guide, so that falsifications of the measuring result cannot occur.

In particular the geometric structure of a tooth as a two-layer system as well as the different optical properties of tooth enamel and dentine as well as their alteration through an alteration of the tooth, as caused by caries or tooth enamel cracks, is utilized according to the invention.

Healthy tooth enamel as the outer shell of a tooth having a layer thickness of typically 0.5-3 mm has a dispersion coefficient in the range of approx. 0.2/mm to 10/mm, and decreases with longer wavelengths. The dispersion coefficient of dentine, on the other hand, is in the range of 2/mm to 80/mm, and likewise decreases with longer wavelengths. The absorption coefficient of tooth enamel is in the range of 0.0003/mm to 0.8/mm and that of dentine is in the range of 0.02/mm to 2/mm, and also decreases with longer wavelengths.

This trend is only reversed in the range of about 1600 nm, since water absorption increases in importance and via local maxima at 2 μm reaches the absolute maximum at 3 μm.

Wavelengths greater than 300 nm and up to 1600 nm are therefore preferred for a high penetration depth. The use of violet or blue light lends itself in order to achieve maximum sensitivity to changes in the dispersion coefficient and the detection of small areas with different dispersion coefficients with localizations in which high penetration depth is not required. For cases with average penetration depths, corresponding wavelengths between these two extremes [are used].

If light is injected (limited locally to the light guide, such as the fiber diameter) via a light guide, such as a glass fiber, which is occlusally placed on the tooth, the light is distributed within the tooth according to the dispersion, absorption and anisotropic coefficients. If the light guide, such as a glass fiber, is placed occlusally vertically on the approximal marginal ridge consisting of tooth enamel, the light scatters mainly within the tooth enamel. However, also in healthy tooth enamel the light is deflected from the original beam direction due to low scattering and can therefore be observed from the buccal or lingual/palatinal side.

The tooth is recorded, that is, measured, by the optical sensor, such as a CMOS, CCD or InGaAs camera, wherein the optical axis of the sensor is preferably vertical to the longitudinal axis of the tooth or orthogonal to the area that is altered, that is, in particular the area having caries. Because light is applied to the tooth according to the invention, the tooth becomes a kind of luminous object as a consequence of the bulk scattering thereof.

This effect is clearly more pronounced when light is injected at a point on the tooth, which only has a low tooth enamel thickness. In the dentine, which is located underneath the enamel layer, the light is much more intensely scattered. Different brightness distributions are thus obtained within the tooth as a function of the injection point. Only limited scattering of the light occurs in other spatial directions if a thick layer of tooth enamel is located under the injection point. This the case if light is injected on the approximal marginal ridge, that is, the border area formed by the tooth enamel, parallel to the approximal wall. If light is guided, however, through a thin enamel layer into the dentine, a kind of diffuse background illumination of the tooth enamel occurs as soon as the light reaches the dentine as a consequence of higher scattering present there.

The first case is suited in particular for approximal caries detection, while the second possibility is suited for smooth surface caries outside the approximal space, and to a limited extent also for fissure caries.

Caries alter the optical properties of the hard tooth tissue. The dispersion coefficient changes above all in the tooth enamel. It increases significantly due to the formation of a porous microstructure in the tooth enamel all the way to a loss of substance with a rough boundary with likewise high light scattering to the remaining enamel. The dispersion coefficient, and also the absorption coefficient, change in the dentine. A clearly visible sign of change of the absorption coefficients is the brownish discoloration of carious dentine.

Caries always start in the tooth enamel in the area of the tooth crown and work their way in the direction of the dentine. The first optically detectable alterations in the tooth enamel are produced in this way as zones with locally clearly increased dispersion coefficients. If the caries reach the dentine, a clear brownish discoloration occurs along the boundary between enamel and dentine due to an increased absorption coefficient, in particular—but not exclusively—in the blue and green spectral ranges.

Caries start generally on so-called predilection areas, among other things in fissures and below the contact point of two teeth. This last case is particularly difficult to diagnose visually, since it eludes direct observation because the gingival papilla cover the interproximal space in the shape of a triangle and the adjacent teeth all stand closely together. However, it is possible to observe the tooth from the vestibular or lingual/buccal side. The dispersion coefficient of the enamel is already so high in the range of the visible light that only limited conclusions about the existence of caries can be drawn from the mere observation under ambient light and also with direct transillumination.

The injection point of the illumination light is varied in order to nevertheless achieve sufficient contrast with vestibular or lingual/buccal observation. If the injection point, with reference to the observation position, is positioned in front of the carious area with an increased dispersion coefficient, this area is illuminated mainly on the observation side by light scatted in the enamel, but also partially directly or indirectly by light scattered at the dentine. An area with a higher dispersion coefficient is therefore visible to the observer (for example, an image scanner or sensor) as a brighter area, because the light is more highly scattered there than in healthy tooth enamel.

If the injection point, with reference to the observation position, is located behind the area of increased scattering, this area is illuminated from the back. This area then appears darker to the observer than if healthy tooth enamel were present at the point of increased scattering, since the light is increasingly scattered away from the observation point in the area of increased scattering. A clear improvement in contrast is achieved if an image is stored with the light injection site in front and behind the caries and these are subtracted one from the other.

In a refinement of this idea, an entire array of fibers can be used in order to enable different light injection points. The optical fibers of an array can also be positioned on both sides of an interproximal area, that is, on the mutually opposite marginal ridges of two adjacent teeth. In this case, an interproximal space can be measured in one measurement. Likewise, a plurality of cameras, for example, buccal and vestibular, can be used at the same time.

A camera can also have a microendoscope optic, which is placed on a point of the tooth that is different from the light injection site.

The images can be recorded sequentially with one light wavelength. They can also be recorded parallel by selecting different wavelengths for different injection points. A plurality of wavelengths can also be applied via each fiber in order to detect absorption differences caused by dentine caries.

The detection of smooth surface caries is carried out by utilizing the dentine as a luminous object. No disruptive surface reflections occur as a consequence of the locally limited light injection by means of a light guide placed on the tooth or located in close proximity to the tooth surface, since the light is reflected directly back into the optical fibers. The light entering the tooth through the tooth enamel is diffusely and homogeneously scattered by the dentine located under the tooth enamel and thus forms background illumination stemming from the tooth. If tooth enamel altered by caries is located in front of it, it is clearly visible as a dark spot in front of a bright background.

The detection of enamel cracks is likewise possible with this procedure, since this acts as a discontinuity during light conduction and illumination in front of the crack and behind the crack will thus cause clearly different light propagation in the tooth with reference to the observation point.

A combination of this procedure with fluorescence detection is likewise possible.

The change of the polarization plane of polarized light through the hard tooth tissue can of course also be utilized.

If the at least one light guide is placed, as preferred, directly on the tooth to be checked or measured, the teaching of the invention is also not abandoned, as mentioned, even if the distance is small; however, this distance must be selected so small that light reflected from the surface passes again into the light guide and does not falsify the measurement.

If the distance can be equal to double the diameter of the light guide core, then the distance should preferably be equal to or smaller than the light guide core diameter itself.

According to the invention, the optical axis of the sensor can be aligned at any arbitrary angle with respect to the tooth in order to perform the measurement. However, the optical axis should preferably run vertically or almost vertically to the longitudinal axis of the tooth.

The front of the light guide, that is, the light injection site, should be placed on or aligned with the occlusal boundary area formed by the tooth enamel, in particular for interproximal caries detection, that is, caries in the approximal space between adjacent teeth. The beam direction of the emergent light should be directed toward the apical side.

A CMOS, CCD or InGaAs camera should preferably be utilized for light detection. When a CCD camera is used, it should have an expanded sensitivity range in the infrared range.

It is also possible to arrange a microendoscope optic in front of the optical sensor, the optic being placed on the tooth in a position that differs from the light injection position or being arranged in the direct vicinity of the tooth surface.

A first measurement should be carried out with the application of light to the occlusal boundary area with reference to the optical sensor behind the tooth alteration, and a second measurement should be carried out with the application of light to the occlusal marginal ridge in front of the tooth alteration, in order to measure the tooth alteration in the approximal space, that is, for interproximal caries detection. The recorded images can be processed in order to draw conclusions about the tooth alteration.

It is also possible to simultaneously measure two adjacent teeth, wherein each tooth has at least one light guide associated with it. At least two light guides can be associated in particular with each tooth, wherein one light guide is arranged in front and one light guide is arranged behind the alteration of the approximal space of the teeth with reference to the optical sensor.

The at least one light guide should be placed on the crown area of the tooth or be aligned therewith in order to determine an alteration of the tooth outside the approximal space, while the optical axis of the sensor is preferably orthogonally aligned with respect to the alteration of the tooth.

The tooth or teeth should especially be subjected to radiation in the wavelength range preferred for light scattering within the enamel layer. The wavelength area should preferably be between 300 nm and 1600 nm, preferably between 350 nm and 1500 nm. Measurements of the absorption changes are advantageous if alterations are detected in the dentine area. In this case, an application of light should take place in at least two wavelength ranges in order to be able to carry out a spectral differential measurement.

Further details, advantages and characteristics of the invention are not only apparent from the claims and the characteristics disclosed therein—separately or in combination—but also from the following description of the preferred embodiments depicted in the drawings.

BRIEF DESCRIPTION OF THE DRAWINGS

The drawings show:

FIG. 1 a schematic diagrams of two teeth in sagittal section;

FIG. 2 an illustration corresponding to FIG. 1 with caries present in the approximal space of the teeth; and FIG. 3 a plan view of the illustration according to FIG. 2.

DESCRIPTION OF THE PREFERRED EMBODIMENTS

FIG. 1 depicts a schematic structure of teeth 10, 12, which are shown in a sagittal section. Each tooth 10, 12 has tooth enamel 14, 16 as an outer layer, which can be up to 3 mm thick. Underneath the tooth enamel 14, 16 the dentine 18, 20 is located, which encloses the tooth nerve (pulp) 22, 24. The gums (gingiva) 28, which have a triangular-shaped geometry between the teeth 10, 12 that closes the intermediate space between the teeth 10, 12, are located over the bone 26. It can also be seen in the illustration that the teeth 10, 12 touch each other in a contact area 30. This area between the teeth 10, 12, which is also called approximal space, is not subject to direct visual control.

Caries form typically underneath the contact point 30 between the teeth 10, 12, whereupon the tooth enamel 14, 16 is initially altered by the caries. The dentine 18, 20 is also altered if the caries continues to progress.

In order to utilize the scattering and absorption properties of tooth enamel 14, 16 and dentine 18, 20 to detect alterations in the tooth 10, 12, in particular the formation of caries, locally limited light is guided, almost injected, into the tooth or teeth 10, 12 according to the invention, whereupon light distribution corresponding to the optical properties of the tooth 10, 12 develops in the tooth volume, wherein said light distribution can then be observed or measured by at least one optical sensor, such as the camera 32.

FIGS. 2 and 3 show a schematic illustration of caries in the approximal space, wherein the caries in the tooth enamel 14 is denoted with the reference numeral 34 and the caries in the dentine 18 is denoted with the reference numeral 36.

Light is guided into the occlusal boundary area 42 formed by the tooth enamel 14 via a light guide 38 or 40 in order to detect or measure the caries 34, 36 on the basis of the teaching of the invention. To this end, the light guide 38, 40 is placed with the light emitting front thereof on the boundary area 42—also called marginal ridge. In this way, it is ensured that no light is reflected by the surface of the tooth 10, 12, which could be detected by the camera, thereby resulting in falsified measurements.

The teaching according to the invention is not abandoned, however, when the light guide 38 or 40 is positioned with the front thereof at a small distance from the marginal ridge 42, but the distance is to be kept so small that the total reflected light is reflected back into the light guide 38 or 40.

It is sufficient for the teaching according to the invention if one of the light guides 38, 40 is used. If, for example, the light guide 40 is placed on the marginal ridge 42 formed by the tooth enamel 14 occlusally and directed in the apical direction, then the light emitted by the light guide 40 is guided mainly into the tooth enamel 14 in the direction of the carious area 34 and is scattered from there in the direction of the optical sensor 32, because the light guide 40 is located in front of the carious alteration 34 with reference to the camera 32. If the light guide 40 is moved into the position corresponding to that of the light guide 38, that is, behind the carious area 34, then the introduced light is scattered away from the camera 32. The radiation scattered away in the direction of the camera 32 (position of the light guide 40) or away from the camera (position of the light guide 38) correlates then with the size of the volume altered by caries.

The carious area 36, which runs in the dentine 18, exhibits not only a corresponding alteration in the tooth enamel 14, as was previously explained, but at the same time also the scattering and absorption behaviors of the dentine 18 have been altered. The added alteration of the absorption coefficient results in differentiation possibilities with regard to reaching the dentine 18 when the illumination is carried out with at least two different wavelengths, which are designed to alter the absorption behavior of the dentine 18 due to the carious area 36 such that absorption changes only minimally at one wavelength if a carious area 36 is present, while absorption differs considerably from healthy dentine 18 at the other wavelength range.

It should be mentioned that light should be basically introduced into the tooth 10, 12 via a single light guide, such as optical fibers. However, the scope of the invention is not abandoned if light is injected via two or three guides. In this case, however, the contrast to be measured could be weakened.

Even if the invention described above is essentially based on a tooth as a body with at least one semitransparent layer, this shall not be considered a limitation. The teaching of the invention rather applies very generally to the measurements of bodies having at least one semitransparent layer, in particular with a two-layer system.

The invention claimed is:

1. A method for detecting alterations on at least one tooth in the dentine and tooth enamel area, comprising:
    providing at least one light guide and an optical sensor,
    capturing light escaping from a front surface of the at least one light guide for impinging at least one tooth,
    recording at least one area of the at least one tooth by the by the optical sensor, and subsequently assessing the image or images determined by the optical sensor;
    wherein, in order to impinge the light from the at least one light guide to the at least one tooth, the from surface of the light guide is placed on the at least one tooth, or positioned at a distance a, with $a \leq 2d$ and d=light guide core diameter, from the surface of the at least one tooth, such that light reflected by the at least one tooth surface is reflected at least substantially exclusively back into the light guide, and the scattered light escaping from the at least one tooth is measured with the optical sensor.

2. The method according to claim 1, wherein the optical sensor is adjusted to the body independently of the light guide.

3. The method according to claim 1, wherein the front of the light guide is positioned at a distance $a \leq d$ from to a surface of the body, or the at least one tooth.

4. The method according to claim 2, wherein the optical axis of the optical sensor is aligned at least almost vertically with respect to the longitudinal axis of the tooth.

5. The method according to claim 1, wherein a main beam direction of the light escaping from the at least one light guide is directed toward the apical side.

6. The method according to claim 2, wherein the front of the light guide is placed on or aligned with an occlusal boundary area formed by the tooth enamel.

7. The method according to claim 1, wherein at least one CMOS, CCD, or InGaAs camera is used as the optical sensor.

8. The method according to claim 2, wherein a microendoscope optic is arranged in front of the optical sensor and is placed on the at least one tooth or is positioned in the direct vicinity of the tooth surface, is arranged in front of the optical sensor.

9. The method according to claim 2, wherein a first measurement is carried out with light applied to an occlusal boundary area behind the tooth alteration, and a second measurement is carried out with light applied to an occlusal marginal ridge in front of the tooth alteration, in order to measure a tooth alteration in an approximal space or for interproximal caries detection.

10. The method according to claim 2, wherein an array of light guides is assigned to the at least one tooth and that one or more light guides of the array are subjected to light having a same wavelength range in order to record or measure the tooth alteration.

11. The method according to claim 2, wherein an array of light guides is assigned to the at least one tooth in that light is simultaneously applied to the light guides of the array in order to record the tooth alteration, wherein into each individual light guide is coupled, having a wavelength range that is different from that of the other light guides.

12. The method according to claim 2, wherein two adjacent teeth are simultaneously measured, wherein at least one light guide is associated with each tooth.

13. The method according to claim 2, wherein at least two light guides are associated with the at least one tooth, wherein one light guide is arranged in front and one light guide is arranged behind the tooth alteration with reference to the optical sensor in an approximal space of the teeth.

14. The method according to claim 2, wherein at least a first image of the at least one tooth with respect to the alteration is recorded with light application in front of the alteration of the at least one tooth or teeth, and at least one second image of the at least one tooth is recorded with light application behind the alteration, and the at least one first image is processed against the at least second image.

15. The method according to claim 2, wherein in order to determine an alteration of the at least one tooth outside an approximal space, at least one light guide is placed on an area of the at least one tooth, or is aligned therewith, and the optical sensor is aligned with the optical axis thereof, substantially orthogonally with respect to the alteration of the at least one tooth.

16. The method according to claim 2, wherein the at least one tooth is subjected to light having a wavelength range $\Delta\lambda$, in which preferentially light scattering occurs in the tooth enamel.

17. The method according to claim 1, wherein the body or the at least one tooth is subjected to light in the wavelength range $\Delta\lambda$ with 300 nm $\leqq \Delta\lambda \leqq$ 1600 nm.

18. The method according to claim 2, wherein spectral differential measurements are carried out in the dentine in order to image the alteration of the at least one tooth.

19. The method according to claim 1, wherein a CCD camera having an expanded sensitivity range in the infrared wavelength range is used as the optical sensor.

* * * * *